(12) United States Patent
Lafontaine et al.

(10) Patent No.: US 8,080,006 B2
(45) Date of Patent: Dec. 20, 2011

(54) METHOD FOR TISSUE CRYOTHERAPY

(75) Inventors: Daniel M. Lafontaine, Plymouth, MN (US); Boaz Avitall, Whitefish Bay, WI (US)

(73) Assignee: Boston Scientific SCIMED, Inc., Maple Grove, MN (US)

( * ) Notice: Subject to any disclaimer, the term of this patent is extended or adjusted under 35 U.S.C. 154(b) by 917 days.

(21) Appl. No.: 12/104,095

(22) Filed: Apr. 16, 2008

(65) Prior Publication Data
US 2008/0208182 A1  Aug. 28, 2008

Related U.S. Application Data

(62) Division of application No. 10/954,136, filed on Sep. 28, 2004, now abandoned.

(51) Int. Cl.
*A61B 18/02* (2006.01)
(52) U.S. Cl. .............. 606/23; 606/21; 606/22
(58) Field of Classification Search ....... 606/20–26
See application file for complete search history.

(56) References Cited

U.S. PATENT DOCUMENTS

| | | | |
|---|---|---|---|
| 5,391,199 A | 2/1995 | Ben-Haim | |
| 5,443,489 A | 8/1995 | Ben-Haim | |
| 5,647,868 A * | 7/1997 | Chinn | 606/21 |
| 6,024,740 A | 2/2000 | Lesh et al. | |
| 6,139,544 A | 10/2000 | Mikus et al. | |
| 6,142,991 A * | 11/2000 | Schatzberger | 606/21 |
| 6,164,283 A | 12/2000 | Lesh | |
| 6,183,468 B1 | 2/2001 | Swanson et al. | |
| 6,235,019 B1 | 5/2001 | Lehmann et al. | |
| 6,241,722 B1 | 6/2001 | Dobak et al. | |
| 6,314,962 B1 | 11/2001 | Vaska et al. | |
| 6,416,511 B1 | 7/2002 | Lesh et al. | |
| 6,432,102 B2 | 8/2002 | Joye et al. | |
| 6,502,576 B1 | 1/2003 | Lesh | |
| 6,514,245 B1 | 2/2003 | Williams et al. | |
| 6,514,249 B1 | 2/2003 | Maguire et al. | |
| 6,527,798 B2 | 3/2003 | Ginsburg et al. | |
| 6,540,740 B2 | 4/2003 | Lehmann et al. | |
| 6,575,966 B2 | 6/2003 | Lane et al. | |
| 6,602,247 B2 | 8/2003 | Lalonde | |
| 6,602,276 B2 | 8/2003 | Dobak, III et al. | |
| 6,648,879 B2 | 11/2003 | Joye et al. | |
| 6,663,622 B1 | 12/2003 | Foley et al. | |
| 6,666,858 B2 | 12/2003 | Lafontaine | |
| 6,685,732 B2 | 2/2004 | Kramer | |
| 6,755,822 B2 | 6/2004 | Reu et al. | |
| 6,893,433 B2 | 5/2005 | Lentz | |
| 2003/0181896 A1 * | 9/2003 | Zvuloni et al. | 606/20 |
| 2003/0199861 A1 | 10/2003 | Lafontaine | |
| 2004/0044334 A1 | 3/2004 | LaFontaine | |
| 2005/0182393 A1 | 8/2005 | Abboud et al. | |
| 2005/0224086 A1 | 10/2005 | Nahon | |

* cited by examiner

*Primary Examiner* — Roy Gibson
(74) *Attorney, Agent, or Firm* — Seager, Tufte & Wickhem, LLC

(57) ABSTRACT

A method for performing cryotherapy on a target tissue region in a body includes positioning a first cooling element in a first location in a body adjacent a target tissue region, positioning a second cooling element in a second location in the body adjacent the target tissue region, and cooling the respective first and second cooling elements so as to cool the target tissue region.

19 Claims, 9 Drawing Sheets

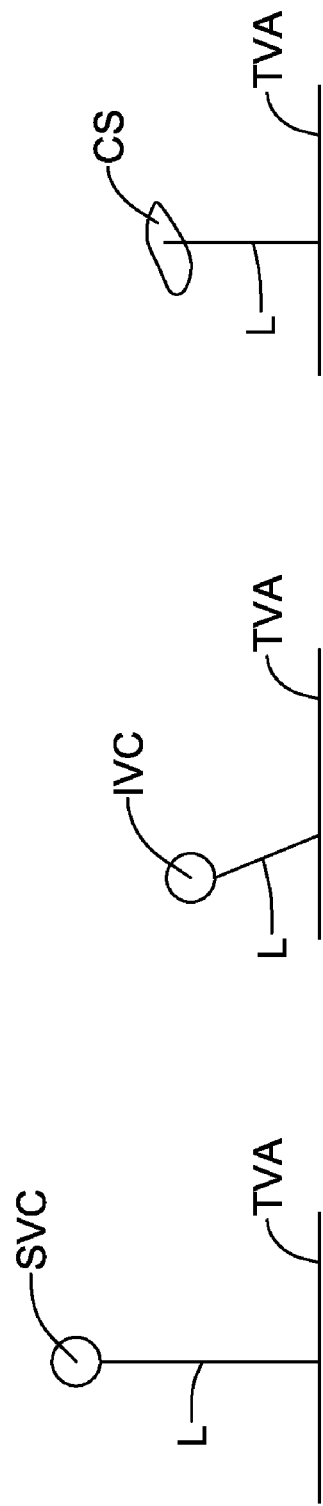

METHOD FOR TISSUE CRYOTHERAPY

RELATED APPLICATIONS

This application is a divisional of U.S. patent application Ser. No. 10/954,136, filed Sep. 28, 2004, now abandoned.

FIELD OF THE INVENTION

The present invention relates generally to therapeutic cooling of body tissue, and more particularly, to methods and apparatus for deploying a plurality of cooling elements to at least partially surround and cool, e.g., to ablate by cryoplasty, a selected tissue region.

BACKGROUND OF THE INVENTION

A number of medical conditions may be treated using ablative techniques or devices. Ablative therapy generally involves the killing of abnormal tissue at an area of interest, thereby resulting in an efficacious treatment for a medical condition. For example, atrial fibrillation may be treatable by ablation of the abnormal tissue within the left atrium and/or the pulmonary vein.

Atrial fibrillation is a serious medical condition that is the result of abnormal electrical activity within the heart. This abnormal activity may occur at regions of the heart including the sino-atrial (SA) node, the atriovenricular (AV) node, or within other areas of cardiac tissue. Moreover, atrial fibrillation may be caused by abnormal activity within one or more isolated focal centers within the heart. It is believed that these foci can originate from within the pulmonary vein, particularly the superior pulmonary veins.

Ablation catheters have been used in minimally invasive techniques to ablate target tissue, e.g., foci having abnormal electrical activity. The techniques typically are characterized by application of energy to create lesions at the foci or other areas possessing abnormal electrical activity. Ablation catheters can also be used to create lesions at the heart to block electrical signals or to alter a travel path of electrical signals at the heart.

Some ablation devices utilize radio frequency (RF) energy for ablation, including the device disclosed in U.S. Pat. No. 6,024,740 to Lesh et al. The RF energy devices may be used to ablate an area of interest with heat. The use of RF energy for ablation may, however, lead to untoward healing responses such as collagen build up at the area of interest after treatment. In some cases, RF ablation may create lesions that cause occlusion of the coronary sinus in post procedure healing. A need, therefore, exists for ablative devices and methods that include improved healing responses.

An alternative treatment strategy has been developed that uses cooling energy for ablation. This method, termed cryoplasty or cryotherapy, may be used to cool or otherwise freeze a portion of target tissue to ablate the target tissue. For example, cryoplasty may be used to cool or freeze and simultaneously dilate a lesion within a blood vessel that might otherwise lead to restenosis or recoil. Cryotherapy may also be used to create lesions at a heart to treat atrial fibrillation. However, creating lesions in a heart using cryotherapy poses a challenge in that it may be difficult to deliver sufficient cooling to create a transmural (i.e., a through thickness) lesion. In addition, blood delivered to and from the heart constantly provides heat to a target site at the heart, thereby counteracting against the cooling being delivered by the cryotherapy, and limiting the amount of cooling that can be delivered to the target site. This in turn, further prevents a transmural lesion, or lesion of a desired size or characteristic, from being created at the target tissue.

Thus, there is currently a need for an improved device and method to perform ablation therapy.

SUMMARY OF THE EMBODIMENTS

In accordance with some embodiments, a method for performing cryotherapy on a target tissue region in a body includes positioning a first cooling element in a first location in a body adjacent a target tissue region, positioning a second cooling element in a second location in the body adjacent the target tissue region, and cooling the respective first and second cooling elements so as to cool the target tissue region.

In accordance with other embodiments, a method for treating atrial fibrillation includes positioning a first cooling element in a patient's coronary sinus adjacent a target tissue region at least partially connecting the patient's left atrium and left ventricle, positioning a second cooling element in the patient's left atrium adjacent the target tissue region, and cooling the respective first and second cooling elements so as to ablate the target tissue region.

In accordance with other embodiments, an apparatus for performing cryotherapy on a target tissue region in a body includes a first cooling element configured for positioning in a first location in a body adjacent a target tissue region, the first cooling element comprising a locatable portion, a second cooling element configured for positioning in a second location in a body adjacent the target tissue region, the second cooling element comprising a locatable portion, each of the first and second cooling elements being in fluid communication with a coolant source, and one or more controllers for controlling cooling of the first and second cooling elements independent of each other.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention. It should be noted that the figures are not drawn to scale and that elements of similar structures or functions are represented by like reference numerals throughout the figures. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 10A-10C show representative lesion patterns in a right atrium that may be formed using the tissue ablation system of FIG. 1.

DETAILED DESCRIPTION OF THE EMBODIMENTS

Figure 1:
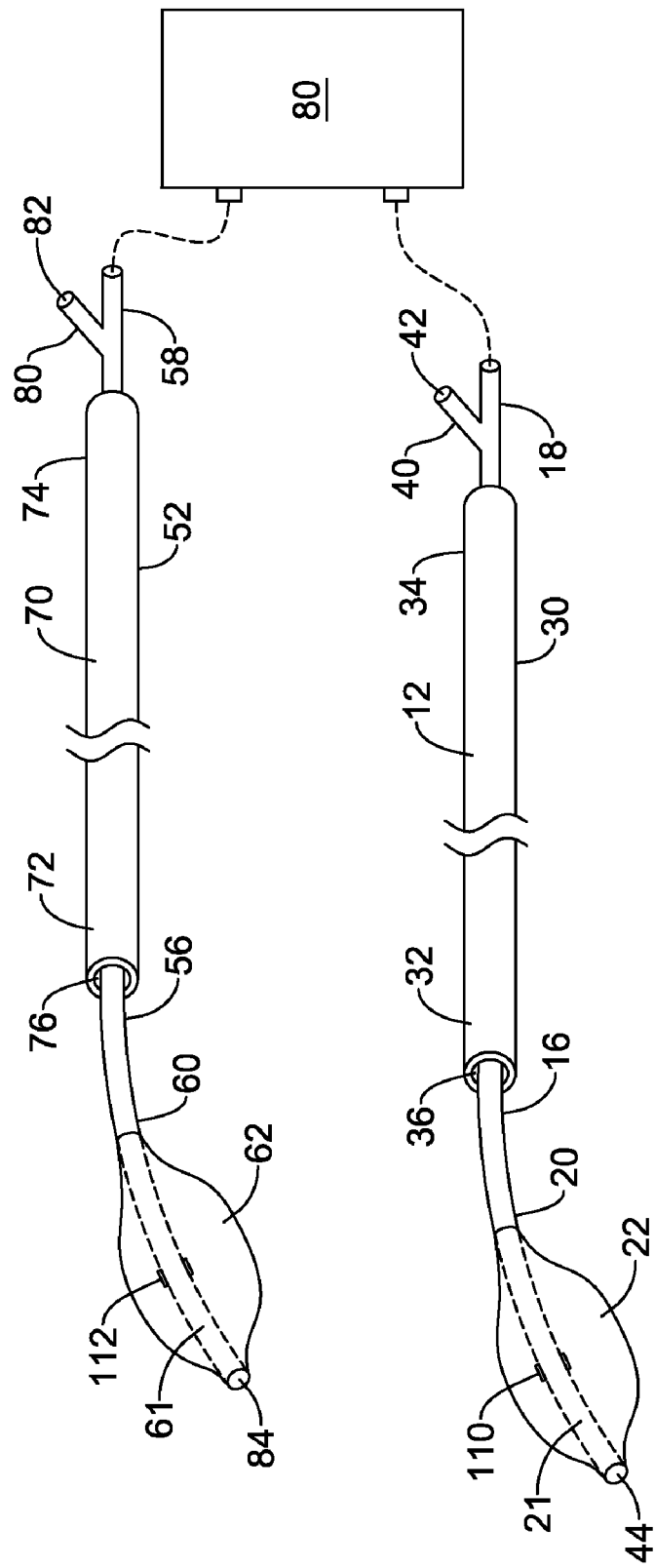
FIG. 1 is a perspective view of a tissue ablation system in accordance with some embodiments of the invention, showing the tissue ablation system having two ablation devices.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments of the invention. They are not intended as an exhaustive description of the invention or as a limitation on the scope of the invention. In addition, an aspect described in conjunction with a particular embodiment of the present invention is not necessarily limited to that embodiment and can be practiced in any other embodiments of the present invention.

FIG. 1 illustrates a tissue ablation system 10 in accordance with some embodiments of the invention. The tissue ablation system 10 includes a first and a second ablation devices 12, 52 configured for introduction into the body of a patient for ablative treatment of target tissue. The tissue ablation system 10 also includes a coolant supply 80 configured for supplying cooling energy to the ablation devices 12, 52 during use. In the illustrated embodiments, the coolant supply 80 provides cooling media to both the first and the second ablation devices 12, 52. Alternatively, each of the first and the second ablation devices 12, 52 can have its own coolant supply.

Figure 2:
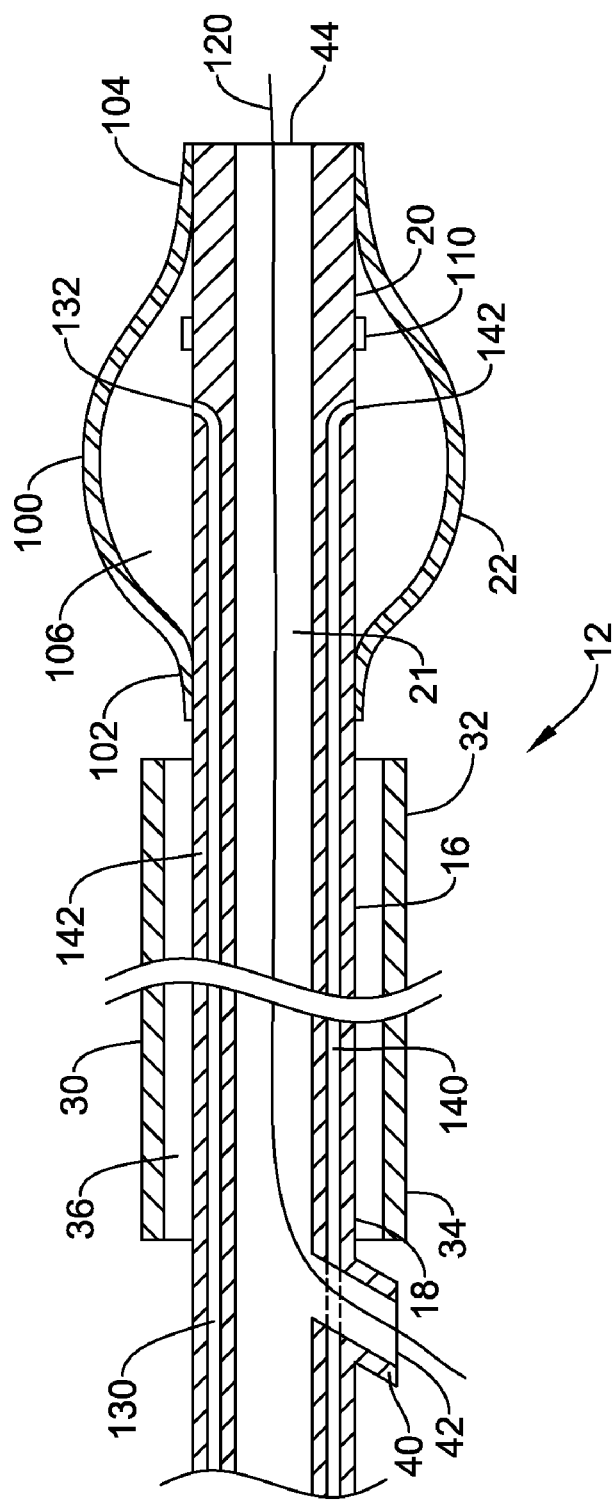
FIG. 2 is a cross sectional view of one of the ablation devices of FIG. 1.

The first ablation device 12 includes a shaft 16 having a proximal end 18, a distal end 20, and a lumen 21 extending between the proximal and the distal ends 18, 20, and terminating at a distal port 44. The proximal end 18 of the shaft 16 has an extension 40 with a guidewire port 42 that is in fluid communication with the lumen 21 of the shaft 16. During use, a guidewire 120 can be inserted through the distal port 44 and exits through the guidewire port 42 at the proximal end 18 of the shaft 16 (FIG. 2). As shown in FIG. 2, the shaft 16 also includes a media delivery channel 130 and a suction channel 140 disposed within a wall 142 of the shaft 16. The media delivery channel 130 and the suction channel 140 extend along the length of the shaft 16 and terminate at a delivery port 132 and a suction port 142, respectively, located at the distal end 20 of the shaft 16. In other embodiments, instead of having the channels 130, 140 within the wall 142 of the shaft 16, the first ablation device 12 can include a fluid delivery tube and a drainage tube. The delivery tube and the drainage tube can be secured to an exterior surface of the shaft 16, or alternatively, be disposed within the lumen 21 of the shaft 16. Also, in other embodiments, a cooling tube having a coil configuration, such as that described in U.S. patent application Ser. No. 10/231,738, can be provided. The entire disclosure of U.S. patent application Ser. No. 10/231,738 is expressly incorporated by reference herein.

The first ablation device 12 also includes a cryo balloon 22. The cryo balloon 22 has a proximal end 102 and a distal end 104 that are both secured to the distal end 20 of the shaft 16, and a lumen 106 that is in fluid communication with the delivery port 132 and the suction port 142. In the illustrated embodiments, the cryo balloon 22 has a configuration that resembles an elliptical shape. Alternatively, the cryo balloon 22 can have other shapes, such as a spherical shape, an elongate shape, or other customized shapes. During use, coolant is delivered from the coolant supply 80 via the media delivery channel 130 and exits through the delivery port 132 to inflate the cryo balloon 22. The delivered coolant can be drained or vacuumed through the suction port 142 to circulate coolant through the cryo balloon 22 and/or to deflate the cryo balloon 22.

In some embodiments, the first ablation device 12 further includes one or more steering wires disposed within the wall 142 of the shaft 16, with the distal end(s) of the steering wire(s) secured to the distal end 20 of the shaft 16. In such cases, tension can be applied to the steering wire(s) to bend the distal end 20 of the shaft 16, thereby steering the cryo balloon 22.

The first ablation device 12 also includes an access cannula 30 having a distal end 32, a proximal end 34, and a lumen 36 extending between the distal and the proximal ends 32, 34. The shaft 16 is located coaxially within the lumen 36 of the cannula 30, and is slidable relative to the cannula 30. During use, the cryo balloon 22 initially in its deflated configuration, is resided within the lumen 36 of the cannula 30. After the distal end 32 of the cannula 30 has been desirably positioned, the shaft 16 is then advanced distally relative to the cannula 30 (or the cannula 30 is retracted proximally relative to the shaft 16) to push the cryo balloon 22 out of the distal end 32 of the cannula 30, and the cryo balloon 22 is then inflated to perform ablative therapy. In some embodiments, the cannula 30 can further include one or more steering wires (not shown) having distal end(s) that is secured to the distal end 32 of the cannula 30. The steering wire(s) can be tensioned to bend the distal end 32, thereby steering the distal end 32 of the cannula 30 during use.

In other embodiments, the first ablation device 12 can further include an outer member (not shown) disposed over the cryo balloon 22. Also, in other embodiments, the first ablation device 12 can further include an outer shaft (not shown) disposed coaxially outside the shaft 16. During use, a vacuum can be created in the lumen that is between the shaft 16 and the outer shaft, thereby providing both thermal insulation and gas isolation between the coolant and the patient. The outer shaft can be made from a biocompatible material known to those skilled in the art of catheter construction, and should be sufficiently rigid to prevent the outer shaft from collapsing when a vacuum is created within the lumen of the outer shaft.

The above and similar devices have been disclosed in U.S. Pat. No. 6,666,858, and U.S. patent application Ser. No. 10/126,027, the entire disclosures of which are expressly incorporated by reference herein.

Returning to FIG. 1, the second ablation device 52 also includes a shaft 56 having a proximal end 58, a distal end 60, and a lumen 61 extending between the proximal and the distal ends 58, 60, and terminating at a port 84. The proximal end 58 of the shaft 56 has an extension 80 with a guidewire port 82 that is in fluid communication with the lumen 61 of the shaft 56. The second ablation device 52 also includes a cryo balloon 62 secured to the distal end 60 of the shaft 56, and an access cannula 70 having a distal end 72, a proximal end 74, and a lumen 76 extending between the distal and the proximal ends 72, 74. The shaft 56 is located coaxially within the lumen 76, and is slidable relative to the cannula 70. The second ablation device 52 is similar to the first ablation device 12, and therefore, will not be described in further details.

The first and the second cryo balloons 22, 62 are adapted to be placed relative to each other such that they at least partially surround a target tissue to be ablated. In the illustrated embodiments, the first and the second ablation devices 12, 52 further include a first element 110 and a second element 112, respectively, for assisting placement of the cryo balloons 22, 62 relative to each other. The first and the second elements 110, 112 can be radio opaque markers that can be visualized under x-ray or fluoroscope. Alternatively, the first and the second elements 110, 112 can be a signal transmitter, and a signal receiver, respectively, or vice versa. For example, the first element 110 can be an ultrasound signal transmitter that transmits ultrasound signals, and the second element 112 can be an ultrasound signal sensor for sensing ultrasound signals. In such cases, based on a time difference between the first element 110 transmitting an ultrasound signal and the second element 112 receiving the ultrasound signal, a distance between the first and the second elements 110, 112 (and therefore, between the cryo balloons 22, 62) can then be determined. Also in other embodiments, multiple receivers could be used to triangulate position(s) of the cryo balloons 22, 62.

In other embodiments, the first element 110 can be a magnet (e.g., a permanent magnet or an electromagnet), and the second element 112 can be a magnetic field sensor, or vice versa. In such cases, based on a sensed magnetic field by the magnetic field sensor, a distance between the cryo balloons 22, 62 can be determined (e.g., a stronger magnetic field indicates that the cryo balloons 22, 62 are closer to each other, and vice versa).

In other embodiments, the first element 110 can be a radiofrequency energy transmitter, and the second element 112 can be a radiofrequency energy sensor, or vice versa. In such cases, based on a strength of the radiofrequency energy sensed by the sensor, a relative distance between the first and the second elements 110, 112 (and therefore, a relative position between the cryo balloons 22, 62) can be determined.

Also, in other embodiments, both the first and the second elements 110, 112 can be magnets (e.g., permanent magnets or electromagnets). In such cases, during use, the magnets mechanically attract the first and the second cryo balloons 22, 62 towards each other, thereby positioning the cryo balloons 22, 62 close to each other. In some embodiments, the cryo balloons 22, 62 are placed on opposite sides of target tissue. In such cases, the magnets will cause the cryo balloons 22, 62 to move towards each other and make contact with opposite sides of the target tissue.

In the above described embodiments, the first and the second elements 110, 112 are secured to the distal ends 20, 60 of the respective shafts 16, 56. Alternatively, the first and the second elements 110, 112 can be secured to the cryo balloons 22, 62, respectively. Furthermore, instead of the first and the second elements 110, 112, in other embodiments, the first and the second ablation devices 12, 52 can include other systems or devices known in the art for determining a relative position or distance between portions of the respective ablation devices 12, 52.

Figure 4:
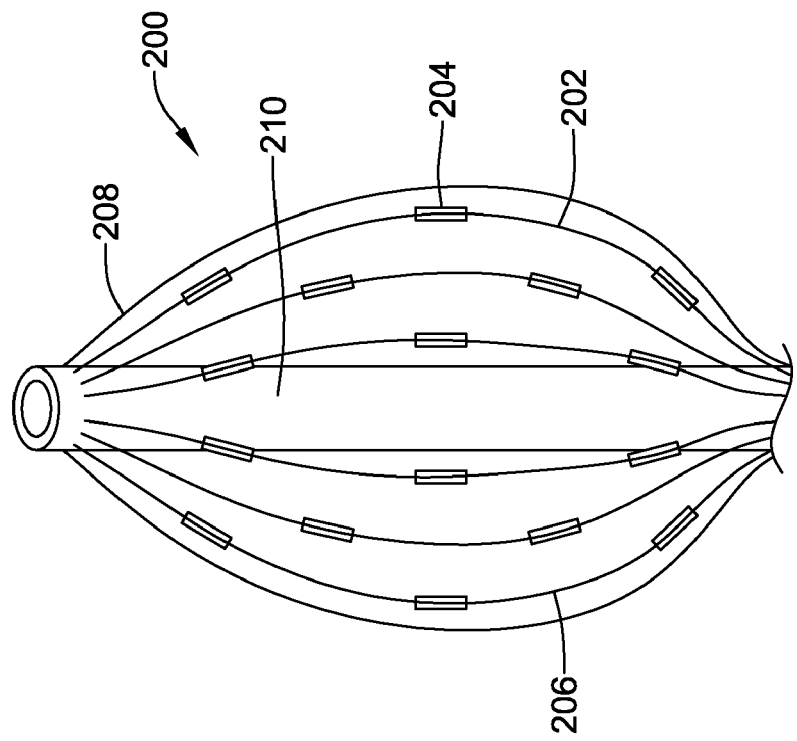
FIG. 4 is a perspective view of a variation of the ablation device of FIG. 3.
Figure 3:
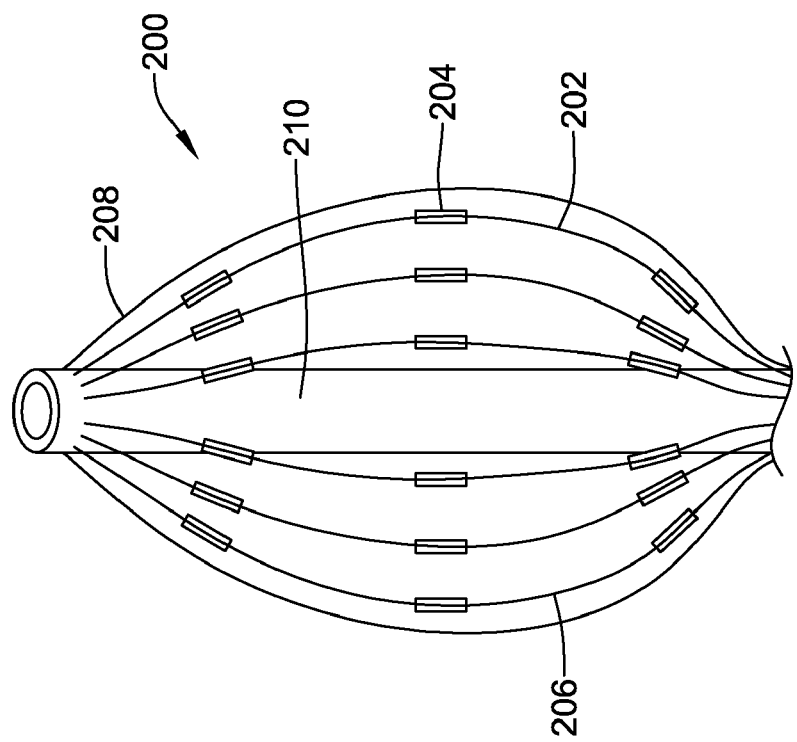
FIG. 3 is a perspective view of an ablation device having an array of sensors in accordance with other embodiments of the invention.

In other embodiments, instead of, or in addition to, having the navigation assisting elements 110, 112, the first and the second ablation devices 12, 52 can each include one or more sensor(s) for sensing a characteristic of target tissue being ablated, a temperature of the cryo balloon, a temperature of the coolant within the lumen of the cryo balloon, and/or a characteristic of an environment in which the tissue is being ablated. FIG. 3 shows an ablation device 200 in accordance with other embodiments of the invention. The ablation device 200 can be used in substitute of either of the ablation devices 12, 52 of FIG. 1. The ablation device 200 includes an array 202 of sensors 204 secured to a cryo balloon 208. The sensors 204 can be, for example, temperature sensors for sensing temperature of tissue being ablated, temperature of the cryo balloon 208, and/or temperature of coolant within the cryo balloon 208. Alternatively, the sensors 204 can be impedance sensors for sensing impedance of tissue being ablated. In other embodiments, the sensors 204 can be other types of sensors for sensing electrical activity of cardiac tissue. In the illustrated embodiments, the array 202 of sensors 204 are secured to an exterior surface of the cryo balloon 208. Alternatively, the sensors 204 can be disposed within a wall of the cryo balloon 208, or be secured to an interior surface of the cryo balloon 208. Also, in other embodiments, the sensors 204 can be secured to the shaft 210. In the illustrated embodiments, the array 202 includes a plurality of splines 206 to each of which, three sensors 204 are secured. In other embodiments, each spline 206 can carry other number of sensors 204. Also, in other embodiments, the array 202 of sensors 204 can be arranged in a staggered configuration (FIG. 4), which allows the sensors 204 to be more uniformly spaced. Although a plurality of sensors 204 are shown, in alternative embodiments, the ablation device 200 can include a single sensor 204. In some embodiments, the sensor 204 can be slidable relative to the shaft 210. For example, the sensor 204 can be slidably coupled to the shaft 210. Alternatively, the sensors 204 can be mounted on an entirely different member (not shown), such as another catheter, that is positionable relative to the shaft 210.

In the illustrated embodiments, the sensors 204 are electrically coupled to a controller (not shown), which is configured to control a temperature of the coolant being delivered to the cryo balloon 208 in response to signals received from the sensors 204. For example, if a sensor 204 senses a temperature indicating that the temperature of the delivered coolant is above a prescribed threshold, the controller then lowers the temperature of the coolant at the source 80 until the temperature of the delivered coolant is within the prescribed threshold. In other embodiments, the controller can be configured to control a flow rate of the coolant being delivered by the source 80 based on signals received from the sensors 204.

Figure 5:
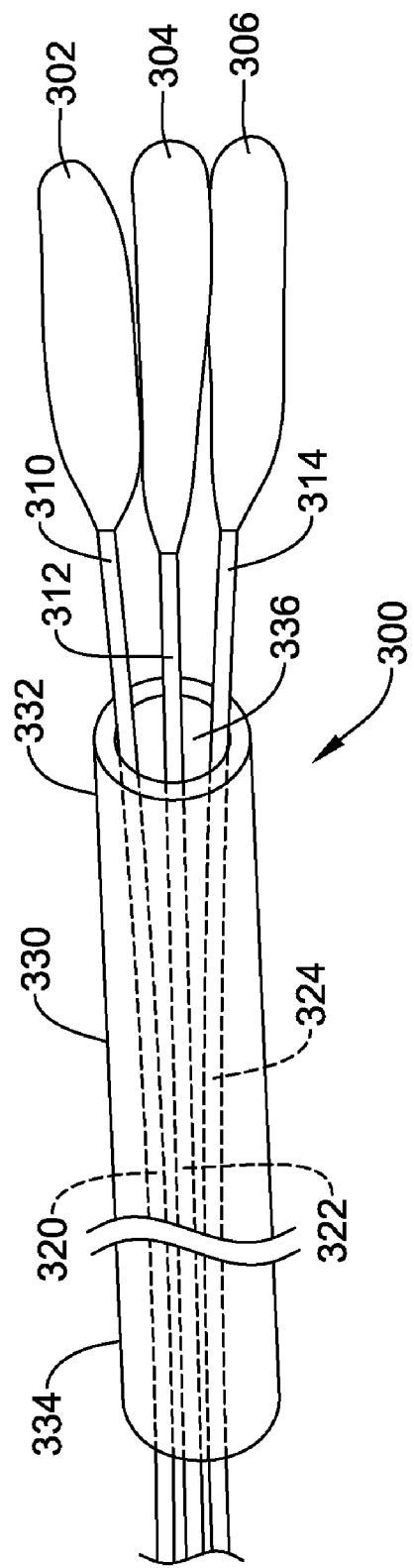
FIG. 5 is a perspective view of a tissue ablation device in accordance with other embodiments of the invention, showing the tissue ablation device having three cryo balloons.
Figure 6B:
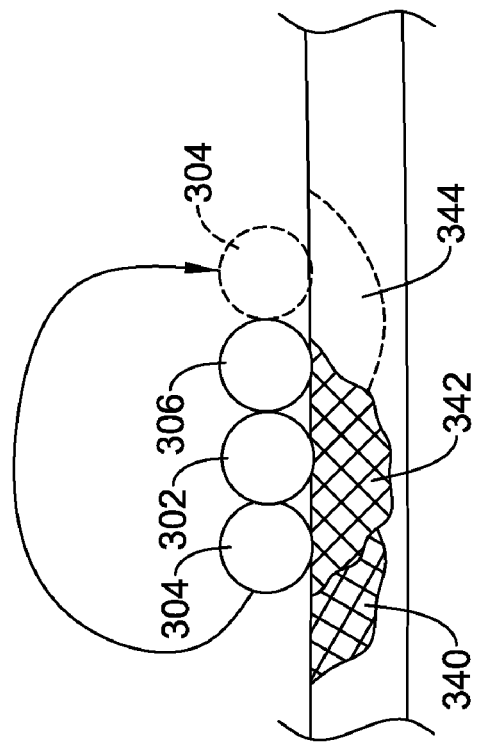
FIGS. 6A and 6B are end views of the tissue ablation device of FIG. 5, showing the tissue ablation device being used to create lesions.
Figure 6A:
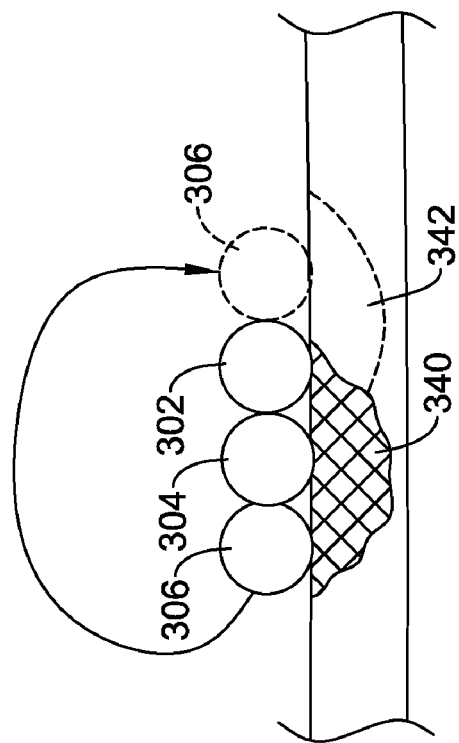

Although the first and the second ablation devices 12, 52 have been described as each having a single cryo balloon, in alternative embodiments, either or both of the ablation devices 12, 52 can each have more than one cryo balloon. FIG. 5 shows an ablation device 300 in accordance with other embodiments of the invention. The ablation device 300 can be used in substitute of either of the ablation devices 12, 52 of FIG. 1. The ablation device 300 has three cryo balloons 302, 304, 306 secured to distal ends 310, 312, 314 of respective shafts 320, 322, 324. The ablation device 300 further includes a cannula 330 having a distal end 332, a proximal end 334, and a lumen 336 extending between the distal and the proximal ends 332, 334. During use, the cryo balloons 302, 304, 306 are pushed out of the distal end 332 of the cannula 330 and are inflated by coolant. The balloons 302, 304, 306 are then placed against target tissue to create a lesion 340 at the target tissue by cryolysis (FIG. 6A). During the ablation procedure, the shafts 320, 322, 324 can be sequentially positioned to place the respective balloons 302, 304, 306 at different target tissue. For example, after the lesion 340 has been created by the balloons 302, 304, 306, the third balloon 306 is then placed adjacent the first balloon 302 to create another lesion 342. While the third balloon 306 is used to create the lesion 342, the first and the second balloons 302, 304 remain in their initial positions to further ablate the target tissue and to increase the size of the first lesion 340. In a similar fashion, the second balloon 304 can next be placed adjacent the third balloon 306 to create another lesion 344 (FIG. 6B). In some embodiments, the shafts 320, 322, 324 can be coupled to an inner tube (not shown) that is disposed within the lumen 336 of the cannula 330. In such cases, the inner tube can be rotated coaxially within the cannula 330 to sequentially place the balloons 302, 304, 306 against different target tissue. As should be understood by those skilled in the art, use of a plurality of balloons is advantageous because it allows target tissue be cooled synergistically.

Figure 7B:
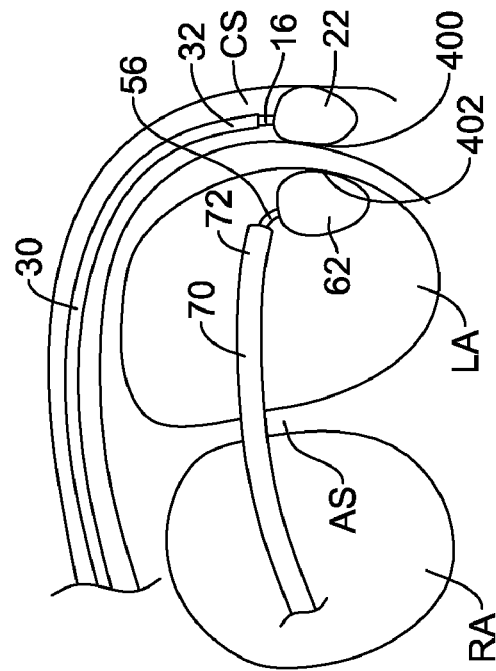
FIGS. 7A and 7B are cross-sectional views, showing a method for treating tissue, in accordance with some embodiments of the invention.
Figure 7A:
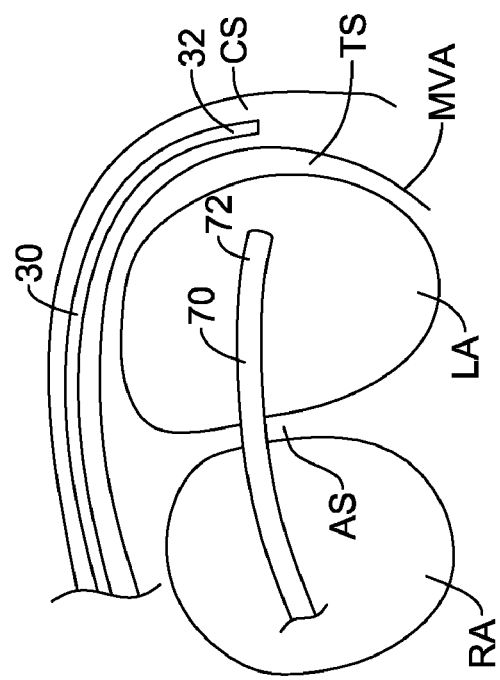

Referring now to FIGS. 7A and 7B, the operation of the tissue ablation system 10 will now be described with reference to cardiac ablation therapy, and more specifically, to creating a lesion at a left atrial isthmus of a heart. However, it should be understood by those skilled in the art that the tissue ablation system 10 can also be used to treat tissue at other locations at the heart, such as an annulus of a mitral valve connecting a left atrium and a left ventricle, or an annulus of a tricuspid valve connecting the an atrium and a right ventricle of the heart. In other embodiments, the tissue ablation system 10 can also be used to treat tissue at other locations within a body.

When using the system 10 to create a lesion at the left atrial isthmus, the first cannula 30 is inserted through the right atrium via jugular or femoral vein access to the vena cava, and is steered into the coronary sinus (CS). The second cannula 70 is also inserted through a main vein, and is steered into a right atrium (RA) of a heart. The cannulas 30, 70 can be steered by using a guidewire in a conventional manner, or by applying tension to steering wire(s) (if the steering wire(s) is provided). After the distal end 72 of the cannula 70 has reached the right atrium, a needle can be inserted into the lumen 76 of the cannula 70 and exits from the distal end 72 to puncture an atrial septum (AS) that separates the right atrium and left atrium (LA). Alternatively, the cannula 70 can be advanced through a guiding sheath placed transeptally into the LA. The distal end 72 of the cannula 70 is then advanced through the atrial septum, and into the left atrium. At the left atrium, the distal end 72 of the cannula 70 is steered to adjacent a treatment site (TS) (FIG. 7A). If the cannula 30, 70 are not steerable, separate cannulas that are steerable, or have a pre-bent configuration, can be used to access the coronary sinus and the left atrium. In such cases, after the separate cannulas have reached the coronary sinus and the left atrium, the cannulas 30, 70 are then inserted into the separate cannulas and are advanced distally until the distal ends 32, 72 exit from the separate cannulas at the coronary sinus and the left atrium, respectively.

Next, the first and the second cryo balloons 22, 62, in their collapsed configuration, are inserted into the lumens 36, 76 of the respective cannulas 30, 70, and are advanced distally within the respective lumens 36, 76 until they reach the distal ends 32, 72 of the cannulas 30, 70. Alternatively, the cryo balloons 22, 62 can be housed within the lumens 36, 76 of the respective cannulas 30, 70 while the cannulas 30, 70 are steered to the treatment site. The cannulas 30, 70 are then retracted relative to the cryo balloons 22, 62 (or the cryo balloons 22, 62 are advanced distally relative to the cannulas 30, 70), thereby exposing the cryo balloons 22, 62.

Next, the cryo balloons 22, 62 are positioned relative to each other such that they are substantially next to each other and are on opposite sides of target tissue. For example, the cryo balloons 22, 62 can be positioned by operating the proximal ends 18, 58 of the respective shafts 16, 56. The cryo balloons 22, 62 can also be steered by using guidewires that are disposed within the respective lumens 21, 61 of the shafts 16, 56 in a conventional manner. If the first and the second ablation devices, 12, 52 include steering wires, tension can be applied to the steering wires to steer the cryo balloons 22, 62, and place the cryo balloons 22, 62 at desired locations. The navigation assisting elements 110, 112 can be used to assist placement of the cryo balloons 22, 62 such that the cryo balloons 22, 62 are substantially next to, or at least proximate, each other on opposite sides of the target tissue. Also, mapping catheter 200 or similar may be used to verify placement.

Next, inflation fluid is delivered under positive pressure by the coolant source 80 to urge the cryo balloons 22, 62 to expand (FIG. 7B). After the first cryo balloon 22 has been expanded, the first cryo balloon 22 substantially occludes the coronary sinus, thereby preventing or substantially reducing flow of blood through the coronary sinus. Such technique is advantageous because it limits the amount of blood that carries heat from passing through target tissue, thereby allowing more cooling energy be delivered to the target tissue. As shown in FIG. 7B, after the cryo balloons 22, 62 have been expanded, the first cryo balloon 22 is in contact with a first surface 400 of target tissue at the left atrial isthmus, and the second cryo balloon 62 is in contact with a second surface 402 that is on an opposite side of the target tissue. If the cryo balloons 22, 62 each includes the sensor(s) 204, the sensor(s) 204 can be used to sense a temperature or an electrical activity to determine whether the cryo balloons 22, 62 are in contact with target tissue to be ablated. The cryo balloons 22, 62 can be further positioned until they are in contact with target tissue to be ablated.

In the illustrated embodiments, the inflation fluid is a low freezing point liquid such as an ethanol mixture, or a liquified gas such as $N_2O$ or $CO_2$. The coolant is one which will provide the appropriate heat transfer characteristics consistent with the goals of treatment. Liquid $N_2O$ can be used as a general purpose coolant, and is particularly useful when freezing of cells is desired. When liquid $N_2O$ is used, it can be transported to the cryo balloons 22, 62 in the liquid phase where it evaporates at the port 132 and exits into the port 142 as a gas. Freon, and other types of gas can also be used as coolants. Other coolants that could be used include cold alcohol/saline solution, Fluisol (a freon based blood substitute), or a mixture of saline solution and ethanol. One skilled in the art would appreciate that other coolants could be used in a similar manner to achieve one or more of the treatment goals. In some embodiments, regulated back pressure may be maintained along the path followed by the coolant in order to prevent freezing of coolant (i.e., dry ice formation) within the respective shafts 16, 56.

After the cryo balloons 22, 62 have been inflated and desirably positioned, the cryo balloons 22, 62 may then be used to cool target tissue to create a cold-induced lesion at the target site. Particularly, the coolant cools the cryo balloons 22, 62, which in turn, cool the target tissue at the left atrial isthmus that is between the cryo balloons 22, 62. In the illustrated embodiments, the target tissue is cooled to a temperature that is approximately between $-20°$ C. to $-100°$ C., and more preferably, between $-40°$ C. to $-80°$ C., such that at least part of the target tissue is ablated by cryolysis. As shown in the illustrated embodiments, by using two cryo balloons that are placed on opposite sides of target tissue to cool the target tissue, sufficient cooling can be delivered to create a transmural (i.e., a through thickness) lesion at the target tissue. It is believed that, by using two cryo balloons (instead of one), synergistic cooling can be delivered to the target tissue, thereby improving the lesion creation process.

In some embodiments, if the second ablation device 52 (or the first ablation device 12) includes the sensor(s) 204, the sensor(s) 204 can be used to sense a temperature or an electrical characteristic of the tissue being ablated during the ablation procedure. The sensor(s) 204 then transmit a signal representative of the sensed temperature or electrical characteristic to a controller (not shown) that is coupled to the source 80 of coolant. In response to the signal, the controller regulates the temperature and/or the flow rate of the coolant that is being delivered to the second cryo balloon 62 (or the first cryo balloon 22). In other embodiments, if the cryo balloons 22, 62 each includes the sensor(s) 204, the controller can independently control the temperatures and/or the flow rates of the coolants that are being delivered to the respective cryo balloons 22, 62.

In many cases, a single ablation may be sufficient to create a desired lesion. However, if it is desired to perform further ablation to increase the lesion size or to create lesions at different site(s) within the treatment region or elsewhere, the cryo balloons 22, 62 may be placed at different target site(s), and the same steps discussed previously may be repeated. When a desired lesion at treatment region has been created, the cryo balloons 22, 62 are deflated and retracted into the respective shaft lumens 36, 76, and the ablation devices 12, 52 are removed from the treatment region.

Figure 8:
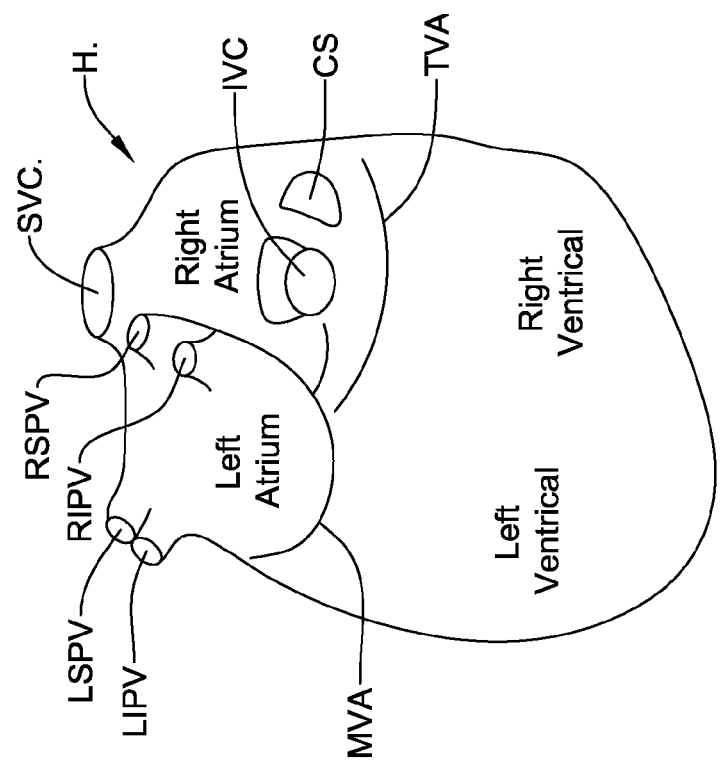
FIG. 8 shows, in diagrammatic form, anatomic landmarks for lesion formation in left and right atriums.
Figure 9B:
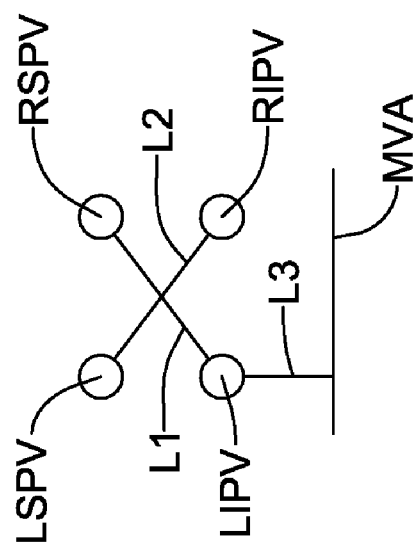
FIGS. 9A and 9B show representative lesion patterns in a left atrium that may be formed using the tissue ablation system of FIG. 1.
Figure 9A:
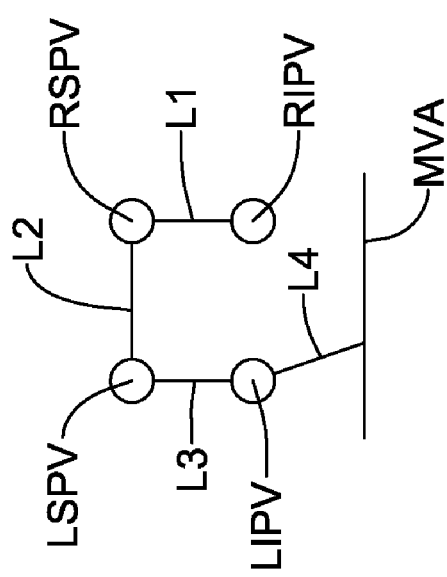

The system 10 and method described previously can be also used to create lesions at other locations of the heart. For example, the system 10 and similar method can be used to create lesions inside the left atrium between the pulmonary veins and the mitral valve annulus. Tissue nearby these anatomic structures are recognized to develop arrhythmia substrates causing atrial fibrillation. Lesions in these tissue regions block reentry paths or destroy active pacemaker sites, and thereby prevent the arrhythmia from occurring. FIG. 8 shows (from outside the heart H) the location of major anatomic landmarks for lesion formation in the left atrium. The landmarks include the right inferior pulmonary vein (RIPV), the right superior pulmonary vein (RSPV), the left superior pulmonary vein (LSPV), the left inferior pulmonary vein (LIPV); and the mitral valve annulus (MVA). FIGS. 9A and 9B show examples of lesion patterns formed inside the left atrium based upon these landmarks.

In FIG. 9, the lesion pattern comprises a first leg L1 between the right inferior pulmonary vein (RIPV) and the right superior pulmonary vein (RSPV); a second leg L2 between the RSPV and the left superior pulmonary vein (LSPV); a third leg L3 between the left superior pulmonary vein (LSPV) and the left inferior pulmonary vein (LIPV); and a fourth leg L4 leading between the LIPV and the mitral valve annulus (MVA). The first, second, and third legs L1-L3 can be created by placing the first cryo balloon 22 at the left atrium (LA), and the second cryo balloon 62 inside the left ventrical (LV), the right ventrical (RV), or the coronary sinus (CS). The fourth leg L4 can be created by placing the first cryo balloon 22 at the LA, and the second cryo balloon 62 inside the CS. In alternative methods, the positions of the first and the second cryo balloons 22, 62 described previously may be exchanged.

FIG. 9B shows a crisscrossing lesion pattern comprising a first leg L1 extending between the RSPV and LIPV; a second leg L2 extending between the LSPV and RIPV; and a third leg L3 extending from the LIPV to the MVA. The first and second legs L1, L2 can be created by placing the first cryo balloon 22 at the LA, and the second cryo balloon 62 inside the LV, RV, or the CS. The third leg L3 can be created by placing the first cryo balloon 22 at the LA, and the second cryo balloon 62 inside the CS. In alternative embodiments, the positions of the first and the second cryo balloons 22, 62 described previously may be exchanged.

The system 10 described previously can also be used to create lesions inside the right atrium. FIG. 8 shows (from outside the heart H) the location of the major anatomic landmarks for lesion formation in the right atrium. These landmarks include the superior vena cava (SVC), the tricuspid valve annulus (TVA), the inferior vena cava (IVC), and the coronary sinus (CS). Tissue nearby these anatomic structures have been identified as developing arrhythmia substrates causing atrial fibrillation. Lesions in these tissue regions block reentry paths or destroy active pacemaker sites and thereby prevent the arrhythmia from occurring.

FIGS. 10A to 10C show representative lesion patterns formed inside the right atrium based upon these landmarks. FIG. 10A shows a representative lesion pattern L that extends between the superior vena cava (SVC) and the tricuspid valve annulus (TVA). The lesion L can be created by placing the first cryo balloon 22 at the LA, and the second cryo balloon 62 inside the LV or the RV. In an alternative embodiment, the positions of the first and the second cryo balloons 22, 62 may be exchanged.

FIG. 10B shows a representative lesion pattern that extends between the interior vena cava (IVC) and the TVA. The lesion L can be created by placing the first cryo balloon 22 at the LA, and the second cryo balloon 62 inside the LV or the RV. In an alternative embodiment, the positions of the first and the second cryo balloons 22, 62 may be exchanged.

FIG. 10C shows a representative lesion pattern L that extends between the coronary sinus (CS) and the tricuspid valve annulus (TVA). The lesion L can be created by placing the first cryo balloon 22 at the right atrium (RA), and the second cryo balloon 62 inside the LV, the RV, or the CS. In an alternative embodiment, the positions of the first and the second cryo balloons 22, 62 may be exchanged.

Although several examples of lesions that can be created using the above-described system have been discussed, the above described system and method can also be used to create lesions at other locations of the heart. For example, in one embodiment, one of the first and the second cryo balloons 22, 62 can be placed at the atrium at the base of a heart, while the other of the first and the second cryo balloons 22, 62 is placed at the LV. Such placement of the first and the second cryo balloons 22, 62 allows a lesion to be created at the intersection of the atria and the ventricle. In another embodiment, one of the cryo balloons 22, 62 can be placed at the RV next to the septum, while the other of the cryo balloons 22, 62 is placed at the LV. Such placement of the cryo balloons 22, 62 allows a lesion to be created at the ventricular septum. In addition, although the above described system and method have been described in the context of cardiac ablation therapy, e.g., for treating arrhythmias, such as ventricular tachycardia (VT), post-myocardial infraction, atrial fibrillation, supra-VT, flutter, and other heart conditions, the system 10 may also be used in many different environments and/or applications. For example, the system 10 may also be used to create lesions, such as transmural lesions, at different locations within the body.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. For example, in alternative embodiments, instead of using cryo balloons, other cooling elements, such as cooling tubes, can be used to deliver cooling energy to ablate target tissue. In addition, an illustrated embodiment needs not have all the aspects or advantages of the invention shown. An aspect or an advantage described in conjunction with a particular embodiment of the present invention is not necessarily limited to that embodiment and can be practiced in any other embodiments of the present invention even if not so illustrated. Thus, the present invention is intended to cover alternatives, modifications, and equivalents that may fall within the spirit and scope of the present invention as defined by the claims.

What is claimed:

1. A method for performing cryotherapy on a target tissue region in a body, comprising:
    positioning a first cooling element in a first location in the body adjacent the target tissue region;
    positioning a second cooling element in a second location in the body adjacent the target tissue region; and
    simultaneously cooling the respective first and second cooling elements so as to create a contiguous lesion in the target tissue region between the first and second locations.

2. The method of claim 1, wherein the first and second positions are on the same surface of the target tissue region.

3. The method of claim 1, further comprising:
    repositioning the first cooling element to a third location on one side of the second location opposite the first location; and
    simultaneously cooling the respective first and second cooling elements so as to expand the contiguous lesion between the first and third locations.

4. The method of claim 3, wherein the second cooling element is maintained at the second position while the respective first and second cooling elements are simultaneously cooled to expand the contiguous lesion between the first and third locations.

5. The method of claim 1, further comprising:
    positioning a third cooling element in a third location in the body adjacent the target tissue region; and
    simultaneously cooling the respective first, second, and third cooling elements so as to create a contiguous lesion between the first, second, and third locations.

6. The method of claim 1, wherein the first location is on one side of an anatomical wall, the second location is on another side of the wall opposite the one side of the anatomical wall, and the contiguous lesion is a transmural lesion through the anatomical wall.

7. The method of claim 1, wherein the target tissue region is a heart tissue region.

8. The method of claim 7, wherein both the first and second locations are inside of the heart.

9. The method of claim 7, wherein the first location is inside of the heart, and the second location is outside of the heart.

10. The method of claim 1, further comprising expanding at least one of the first and second cooling elements.

11. The method of claim 1, wherein the target tissue region is proximate an annulus of a mitral valve connecting a left atrium and left ventricle of a heart.

12. The method of claim 11, wherein the target tissue region comprises a left atrial isthmus of the heart.

13. The method of claim 1, wherein the target tissue region is proximate an annulus of a tricuspid valve connecting a right atrium and right ventricle of a heart.

14. The method of claim 1, wherein the first location is in a coronary sinus and the second location is in a left atrium.

15. The method of claim 14, wherein positioning the first cooling element in the coronary sinus comprises:
    inserting the first cooling element in the coronary sinus when the first cooling element is in a collapsed profile; and
    expanding the first cooling element to an expanded profile that substantially occludes the coronary sinus.

16. The method of claim 1, wherein one or both of the first and second locations comprises an atrium or ventricle of a heart.

17. The method of claim 1, wherein one of the first and second location comprises a pulmonary vein or pulmonary vein opening.

18. The method of claim 1, wherein positioning of the first cooling element comprises locating a portion of the first cooling element and verifying that the located portion is in contact with, or otherwise adjacent to, the target tissue region.

19. The method of claim 1, wherein cooling the first and second cooling elements comprises conveying a coolant to the respective first and second cooling elements, and controlling a temperature and/or flow rate of the conveyed coolant.

* * * * *